United States Patent [19]

Kurath et al.

[11] 4,338,308

[45] Jul. 6, 1982

[54] 4-N-β-LYSYL-2'-N-DES-β-LYSYL ANTIBIOTIC AX-127B-1 AND THE PHARMACEUTICALLY ACCEPTABLE SALTS THEREOF

[75] Inventors: Paul Kurath, Waukegan; Earl E. C. Fager, Lake Villa, both of Ill.

[73] Assignee: Abbott Laboratories, North Chicago, Ill.

[21] Appl. No.: 205,814

[22] Filed: Nov. 10, 1980

[51] Int. Cl.³ .................... A61K 31/71; C07H 15/22
[52] U.S. Cl. ................................ 424/180; 424/181; 435/80; 536/16.8
[58] Field of Search .................. 536/17 B, 17 R; 424/180, 181

[56] References Cited

U.S. PATENT DOCUMENTS 4,091,032  5/1978  Tadanier et al. .............. 536/17 R
4,187,299  2/1980  Post ............................. 536/17 R
4,241,182  12/1980  Takasawa et al. ............. 536/17 R
4,283,529  8/1981  Rosenbrook, Jr. ............. 424/180

OTHER PUBLICATIONS

Rinehart, Jr. et al., "Aminocyclitol Antibiotics", 1980, pp. 309–320.
Tadanier et al., "Carbohydrate Research", vol. 79, pp. 91–102, vol. 85, pp. 61–71, 1980.

*Primary Examiner*—Johnnie R. Brown
*Attorney, Agent, or Firm*—Joyce R. Niblack; Gildo E. Fato; Dennis K. Shelton

[57] ABSTRACT

4-N-Lysyl-2'-N-des-β-lysyl antibiotic AX-127B-1 and the pharmaceutically acceptable salts thereof. The compounds are useful as intermediates in the preparation of 3-O-demethyl 4-N-lysyl-2'-N-des-β-lysyl antibiotic AX-127B-1 and as a broad spectrum antibacterial agents.

2 Claims, No Drawings

4-N-β-LYSYL-2'-N-DES-β-LYSYL ANTIBIOTIC AX-127B-1 AND THE PHARMACEUTICALLY ACCEPTABLE SALTS THEREOF

BACKGROUND OF THE INVENTION

Antibiotic AX-127B-1 is a relatively new aminoglycoside antibiotic. (Commonly assigned, co-pending U.S. Ser. No. 008,378, filed Feb. 1, 1979).

Chemical modification of the aminoglycoside antibiotics, as with other classes of antibiotics, has been found to improve the activity, either intrinsic or against resistant strains of organisms, or to reduce the toxicity of the parent antibiotics. And, because of the development of aminoglycoside-resistant strains and inactivation of the parent antibiotics by R-mediated factors which can develop, the search continues for new entities which are either superior to known aminoglycosides or which provide an alternative therapy when resistant organisms develop.

In a related family of aminoglycoside antibiotics, the fortimicins, 3-O-demethylation has been found to improve the intrinsic activity of the antibiotics. See, for example, U.S. Pat. No. 4,124,756.

3-O-demethyl-antibiotic AX-127B-1 and its 4-N-alkyl and acyl derivatives are disclosed and claimed in commonly assigned, co-pending U.S. Ser. No. 126,732, filed Mar. 3, 1980, now U.S. Pat. No. 4,283,529. The present invention provides one derivative of antibiotic AX-127B-1 which is useful as an intermediate in the preparation of the corresponding 3-O-demethyl derivatives of AX-127B-1, and as an antibiotic and anti-bacterial agent.

SUMMARY

The present invention provides 4-N-β-lysyl-2'-N-des-β-lysyl antibiotic AX-127B-1 and the pharmaceutically acceptable salts thereof. The compound is useful as an intermediate in the preparation of the corresponding 3-O-demethyl derivatives of AX-127B-1, 3-O-demethyl-4-N-β-lysyl-2'-N-des-β-lysyl antibiotic AX-127B-1.

DETAILED DESCRIPTION OF PREFERRED EMBODIMENTS

Antibiotic AX-127B-1 is represented by the formula:

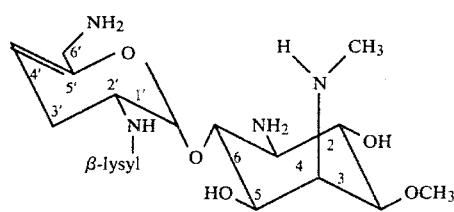

The compound of this invention, 4-N-β-lysyl-2'-N-des-β-lysyl AX-127B-1 is represented by the formula:

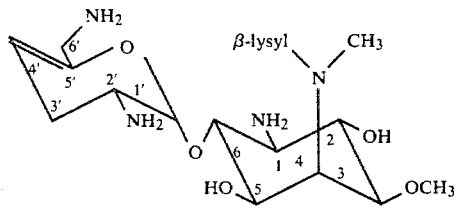

and the pharmaceutically acceptable salts thereof.

The term "pharmaceutically acceptable salts" refers to the non-toxic acid addition salts which can be prepared either in situ during the final isolation and purification or by separately reacting the free base with a suitable organic or inorganic acid by methods well known in the art. Representative salts include the mono or per salts such as the hydrochloride, hydrobromide, sulfate, bisulfate, tetrahydrochloride, acetate, oxalate, valerate, oleate, palmitate, stearate, laurate, borate, benzoate, lactate, phosphate, tosylate, citrate, maleate, fumarate, succinate, tartate, napsylate, and the like.

4-N-β-lysyl-2'-N-des-β-lysyl antibiotic AX-127B-1, in addition to its use as a valuable intermediate in the preparation of 3-O-demethyl-4-N-β-lysyl-2'-N-des-β-lysyl AX-127B-1, is useful as an antibacterial agent against susceptible strains of gram negative and gram positive bacilli such as *Staphylococcus aureus, Escherichia coli, Psuedomonas aeruginosa, Bacillus subtilis, Proteus vulgaris, Shigella sonnei, Salmonella typhi,* and *Klebsiella pneumoniae.*

The term "susceptible strains" refers to strains of bacilli or organisms which have been demonstrated to be sensitive to a particular antibiotic in a standard in vitro sensitivity test and thus in vitro activity has been established for a particular antibiotic against a specific strain of a particular organism.

The antibiotic of this invention is administered parenterally, i.e., intravenously, intramuscularly, intraperitoneally, or subcutaneously for systemic effect in daily dosages of from about 30 to about 120 mg/kg of body weight daily, preferably from about 50 to 80 mg/kg of body weight daily, based on lean body weight. It is further preferred to administer the antibiotic in divided daily dosages. Oral administration to sterilize the intestinal tract is also contemplated by the present invention.

The compound of this invention can be O-demethylated to provide the corresponding O-demethyl derivative of antibiotic AX-127B-1 by dissolving the compound to be O-demethylated in, for example, methylene chloride, cooling the reaction mixture to a temperature of from about −72° C. to about 30° C., preferably about 0° C., and treating the reaction mixture with from about 10 to about 100 equivalents of a boron trihalide, preferably boron tribromide, with stirring, for about 10 to about 60 minutes at temperatures of between −72° C. to 100° C., preferably from about −4° C. to about 38° C. Solvent and residual boron trihalide are removed in vacuo, the reaction mixture is treated with an appropriate solvent such as methanol to remove residual solvent and boron trihalide and evaporated to a residue to provide the desired derivative.

The following examples further illustrate the present invention:

EXAMPLE 1

Culture AB-127B-46 was maintained on ATCC medium #172 agar slants consisting of 1% glucose, 2% soluble starch, 0.5% Difco yeast extract, 0.5% N-Z amine type A (Sheffield Chemical Co.), 0.1% $CaCO_3$, 1.5% agar, and distilled water QS to 1 liter.

First passage inoculum seed tubes (25×150 mm) containing 10 ml of sterile S-3 seed medium (Table 1), and closed with Bellco stainless steel caps, were inoculated with a sterile loop from ATCC medium #172 agar slant cultures of AB-127B-46. Seed tubes were incubated on a rotary shaker (250 r.p.m.) at 30° C. for 96 hours. At that time 5% vegetative inoculum from the first passage seed tube was transferred aseptically to 500 ml Erlenmeyer flasks containing 100 ml of sterile S-3 seed medium and closed with cotton plugs. Inoculated second passage seed flasks were then incubated on a rotary shaker (250 r.p.m.) at 30° C. for 72 hours. Antibiotic production fermentation flasks (500 ml Erlenmeyer) containing 100 ml of sterile AFIb medium (Table 1) and closed with cotton plugs were inoculated with 5% vegetable inoculum from the second passage seed flasks.

The innoculated AFIb antibiotic production medium flasks were then incubated on a rotary shaker (250 r.p.m.) at 30° C. for 5 to 7 days and then harvested.

The harvested whole culture fermentation beer from a series of flasks was pooled (30 liters), adjusted to pH 2 with sulfuric acid and clarified by centrifugation or by filtration through celite. The clarified fermentation liquor was then poured into a 6.5 cm diameter glass column containing 0.7 liters of AMBERLITE IRC 84 cation exchange resin (ammonia form). The active antibiotic was adsorbed on the resin and the effluent beer was discarded. The resin column was washed thoroughly with water. Antibiotic activity was then eluted with 1 N aqueous ammonia. Active fractions were determined by dipping paper discs in eluate fractions and testing for activity on agar plates seeded with *Staphylococcus aureus* ATCC 6538P. Active fractions were combined and concentrated to remove excess ammonia and were then neutralized to pH 6.5 with sulfuric acid. The concentrate was then passed through a glass column containing REXYN 102 ion exchange resin ($NH_4+$) 2 cm diameter×6 cm in height or 18 ml of resin. The column was washed with water and then eluted by stepwise gradient with aqueous ammonia starting with 0.05 N and increasing to 1 N ammonia.

Active fractions were again located by the paper disc method and further examined by both paper chromatography and thin-layer chromatography as previously described. Active fractions containing the antibiotic described in this invention were combined, concentrated to remove excess ammonia, neutralized to pH 6.5 with sulfuric acid and reduced to dryness under vacuum. The sulfate salt of the antibiotic was dissolved in a distilled water and converted to free base by passing through a small glass column containing DOWEX 1-X2 ion exchange resin ($OH^-$).

TABLE 1

| S-3 Seed Medium | |
|---|---|
| Ingredient | gm/liter |
| Staclipse J soluble starch (Staley) | 24 |
| glucose monohydrate | 1 |
| yeast extract (Difco) | 5 |
| tryptone (Difco) | 5 |
| beef extract (Wilson) | 3 |
| $CaCO_3$ | 4 |
| tap water QS to 1.0 liter | |
| sterilization: 30 min., 121° C. at 15-16 lb. pressure | |

| AFIb Fermentation Medium | |
|---|---|
| Ingredient | gm/liter |
| glucose monohydrate | 10 |
| peptone (Difco) | 5 |
| yeast extract (Difco) | 5 |
| $CaCO_3$ | 1 |
| pH 7.3 | |
| tap water QS to 1.0 liter | |
| sterilization: 30 min., 121° C. at 15-16 lb. pressure | |

EXAMPLE 2

Culture AB-127B-46 was inoculated into first passage 500 ml Erlenmeyer seed flasks containing 100 ml of sterile S-3 seed medium and closed with cotton plugs. Inoculated flasks were incubated on a rotary shaker (250 r.p.m.) at 30° C. for 96 hours. At that time, 5% vegetative inoculum was transferred into similar 500 ml Erlenmeyer flasks containing 100 ml of sterile S-3 seed medium. Inoculated second passage seed flasks were incubated on a rotary shaker at 30° C. for 72 hours. Second passage seed flasks were used to inoculate a series of 30 liter stainless steel fermentors at a level of 5% inoculum. Fermentation conditions for 30 liter fermentors were as follows:

| | |
|---|---|
| Fermentation Medium: | AfIb (see Table 5) |
| Fermentor Volume: | 12 liters |
| Sterilization Time: | 1 hr., 121° C., 15-16 lb pressure |
| Antifoam: | .01% P-2000 polyethylene glycol (Dow Chemical Co.) |
| Incubation Temp.: | 30° C. |
| Agitation: | 250 r.p.m. |
| Impeller Blade Angle: | 45° |
| Air Rate: | 1 volume/volume/min. |

Fermentors were incubated for 5 days and then harvested. The desired antibiotic described in this invention was isolated and purified as described in the Example 1.

EXAMPLE 3

2'-N-Des-β-lysyl-antibiotic AX-127B-1

A total of 4.66 g of the sulfate salt of antibiotic AX-127B-1 sulfate salt (prepared according to the procedure of Example 1) is converted to the free base by treatment with AG 2×8 resin ($OH^-$) form, BioRad Laboratories, to afford 2.71 g of the free base after lyophilization. Raman spectrum $\nu_{max} 1690^{-1}$. The latter is refluxed gently in 25 ml of hydrazine hydrate for 22 hours. Evaporation of the hydrazine leaves a residue of 2.755 g of crude product. The crude product is chromatographed on 140 g of silica gel in the lower phase of methanol-methylene chloride-ammonium hydroxide [1:1:1(v/v/v)]. Ten ml fractions are collected and a total of 1.325 g of product is obtained.

EXAMPLE 4

2'-N-Des-β-lysyl-1,2',6'-tri-N-o-nitrobenzyloxycarbonyl-antibiotic AX-127B-1

To a stirred solution of 2'-N-des-β-lysyl antibiotic AX-127B-1 (2.0 g), water (30 ml) and methanol (60 ml), cooled in an ice bath at 0° C., are added 4.44 g of o- nitrobenzyloxycarbonyloxysuccinimide. Stirring is continued for 3 hours at 0° C. and then at ambient temperature for 22 hours. The major portion of the methanol is evaporated under reduced pressure and the residue shaken with a mixture of chloroform and water. The chloroform solution is washed with water and dried over anhydrous magnesium sulfate. The chloroform is evaporated and the residue is chromatographed on silica gel packed and eluted with a solvent system composed of chloroform-methanol-concentrated ammonium hydroxide [23.4:1.4:0.1(v/v/v)] to yield the desired intermediate.

EXAMPLE 5

4-N-β-lysyl-2'-N-des-β-lysyl-penta-N-o-nitrobenzyloxycarbonyl antibiotic AX-127B-1

To a magnetically stirred solution of 1.0 g of 2'-N-des-β-lysyl-1,2',6'-tri-N-o-nitrobenzyloxycarbonyl antibiotic AX-127B-1, 0.4 g of N,N'-di-(o-nitrobenzyloxycarbonyl)-β-lysine and 0.4 g of 1-hydroxybenzotriazole monohydrate in 2.8 ml of tetrahydrofuran, cooled in an ice bath, is added a solution of 0.35 g of N,N-dicylohexylcarbodimide in 2.8 ml of tetrahydrofuran. Stirring is continued at 0° C. for 1 hour and then at ambient temperature for 18 hours. The precipitated N,N'-dicyclohexylurea is removed by filtration and the tetrahydrofuran evaporated under reduced pressure. Purification is effected by chromatography on silica gel.

EXAMPLE 6

4-N-β-Lysyl-2'-N-des-β-lysyl antibiotic AX-127B-1

4-N-β-Lysyl-2'-N-des-β-lysyl-penta-N-o-nitrobenzyloxycarbonyl antibiotic AX-127B-1 is dissolved in ethanol, the solution is placed under an ultra-violet light source for 24 hours. The ethanol is evaporated to leave the desired product.

EXAMPLE 7

4-N-β-Lysyl-2'-N-des-β-lysyl antibiotic AX-127B-1 tetrahydrochloride

4-N-β-Lysyl-2'-N-des-β-lysyl-penta-N-o-nitrobenzyloxycarbonyl antibiotic AX-127B-1 is deprotected in methanolic hydrochloric acid following the procedure of Example 5 to obtain the pentahydrochloride salt.

EXAMPLES 8–27

By substituting the desired acid in the method of Example 6 or reacting 4-N-β-lysyl-2'-N-des-β-lysyl antibiotic AX-127B-1 with the desired acid in an appropriate solvent, the following representative per salts are obtained:

4-N-β-lysyl-2'-N-des-β-lysyl antibiotic AX-127B-1 pentahydrobromide;
4-N-β-lysyl-2'-N-des-β-lysyl antibiotic AX-127B-1 sulfate;
4-N-β-lysyl-2'-N-des-β-lysyl antibiotic AX-127B-1 acetate;
4-N-β-lysyl-2'-N-des-β-lysyl antibiotic AX-127B-1 oxalate;
4-N-β-lysyl-2'-N-des-β-lysyl antibiotic AX-127B-1 valerate;
4-N-β-lysyl-2'-N-des-β-lysyl antibiotic AX-127B-1 oleate;
4-N-β-lysyl-2'-N-des-β-lysyl antibiotic AX-127B-1 palmitate;
4-N-β-lysyl-2'-N-des-β-lysyl antibiotic AX-127B-1 stearate;
4-N-β-lysyl-2'-N-des-β-lysyl antibiotic AX-127B-1 laurate;
4-N-β-lysyl-2'-N-des-β-lysyl antibiotic AX-127B-1 borate;
4-N-β-lysyl-2'-N-des-β-lysyl antibiotic AX-127B-1 benzoate;
4-N-β-lysyl-2'-N-des-β-lysyl antibiotic AX-127B-1 lactate;
4-N-β-lysyl-2'-N-des-β-lysyl antibiotic AX-127B-1 phosphate;
4-N-β-lysyl-2'-N-des-β-lysyl antibiotic AX-127B-1 tosylate;
4-N-β-lysyl-2'-N-des-β-lysyl antibiotic AX-127B-1 citrate;
4-N-β-lysyl-2'-N-des-β-lysyl antibiotic AX-127B-1 maleate;
4-N-β-lysyl-2'-N-des-β-lysyl antibiotic AX-127B-1 fumarate;
4-N-β-lysyl-2'-N-des-β-lysyl antibiotic AX-127B-1 succinate;
4-N-β-lysyl-2'-N-des-β-lysyl antibiotic AX-127B-1 tartrate;
4-N-β-lysyl-2'-N-des-β-lysyl antibiotic AX-127B-1 napsylate, etc.

The present invention includes within its scope pharmaceutical compositions comprising, as an active ingredient, 2'-N-des-β-lysyl-antibiotic AX-127B-1 or a pharmaceutically acceptable carrier or diluent. The compounds are administered parenterally (i.e., by intramuscular, intravenous, intraperitoneal or subcutaneous routes of injection) or, to sterilize the gastrointestinal tract, by oral routes of administration, and can be formulated in dosage forms appropriate for each route of administration.

Solid dosage forms for oral administration include capsules, tablets, pills, powders and granules. In such solid dosage forms, the active compound is admixed with at least one inert carrier or diluent such as sucrose, lactose or starch. Such dosage forms can also comprise buffering agents. Tablets and pills can additionally be prepared with enteric coatings.

Liquid dosage forms for oral administration include pharmaceutically acceptable emulsions, solutions, suspensions, syrups and elixirs, containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectible medium immediately before use.

The dosage of the active ingredient in the composition may be varied to accomodate pediatric dosages, adult dosages, etc. However, it is necessary that the amount of active ingredient shall be such that a suitable dosage form is obtained.

The following examples further illustrate the present invention.

EXAMPLE 28

Tablets weighing 500 mg and having the following composition are formulated:

| Ingredient | Mg |
|---|---|
| 4-N-β-lysyl-2'-N-des-β-lysyl antibiotic AX-127B-1 | 250 |
| Starch | 200 |
| Colloidal silica | 44 |
| Magnesium stearate | 6 |

EXAMPLE 29

Sterile 25 ml ampules are prepared containing 20 mg/ml of 4-N-β-lysyl-2'-N-des-β-lysyl antibiotic AX-127B-1 hydrochloride, 0.1 percent sodium bisulfate, 0.7 percent sodium chloride, 0.5 percent chlorobutanol and water q.s.

I claim:
1. 4-N-β-Lysyl-2'-N-Des-β-lysyl-antibiotic AX127B-1 or a pharmaceutically acceptable salt thereof.
2. A pharmaceutical composition comprising an antibacterially effective amount of a compound of claim 1 and a pharmaceutically acceptable carrier or diluent.

* * * * *